United States Patent
Sakamoto et al.

(10) Patent No.: US 10,098,654 B2
(45) Date of Patent: Oct. 16, 2018

(54) ARTHROENDOSCOPICAL SURGICAL METHOD

(71) Applicant: OLYMPUS CORPORATION, Tokyo (JP)

(72) Inventors: Takamitsu Sakamoto, Hachioji (JP); Chie Onuma, Tama (JP); Ken Fujisaki, Sagamihara (JP); Kiichiro Sawada, Hachioji (JP); Kazuhiro Yoshida, Sagamihara (JP); Satoshi Takekoshi, Hachioji (JP); Sohei Ueda, Tokyo (JP); Yasuo Tanigami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 26 days.

(21) Appl. No.: 15/082,625

(22) Filed: Mar. 28, 2016

(65) Prior Publication Data

US 2017/0273707 A1 Sep. 28, 2017

(51) Int. Cl.
*A61B 17/16* (2006.01)
*A61B 17/32* (2006.01)
(Continued)

(52) U.S. Cl.
CPC .. *A61B 17/320016* (2013.01); *A61B 1/00087* (2013.01); *A61B 1/043* (2013.01);
(Continued)

(58) Field of Classification Search
CPC ............ A61B 1/00186; A61B 1/00096; A61B 1/00163; A61B 1/00165; A61B 1/00167; A61B 1/0017; A61B 1/00172; A61B 1/002; A61B 1/04; A61B 1/042; A61B 1/045; A61B 1/043; A61B 1/05; A61B 1/051; A61B 1/055; A61B 1/06; A61B 1/0638; A61B 1/0646; A61B 1/0653; A61B 1/07; A61B 1/313; A61B 1/3132; A61B 1/3135; A61B 1/317; A61B 17/1659; A61B 17/16; A61B 17/1675; A61B 17/1677;
(Continued)

(56) References Cited

U.S. PATENT DOCUMENTS

2010/0191173 A1* 7/2010 Kimura .......... A61B 17/320068
604/21
2013/0338792 A1* 12/2013 Schmieding ........ A61F 2/30756
623/23.73
(Continued)

FOREIGN PATENT DOCUMENTS

JP WO 2015087839 A1 * 6/2015 ......... A61K 49/0002

*Primary Examiner* — Ryan Henderson
(74) *Attorney, Agent, or Firm* — Oliff PLC (57) ABSTRACT

An arthroscopical surgical method using an ultrasonic treatment device for a joint includes: transmitting ultrasonic vibration to a treatment portion of the ultrasonic treatment device, removing an injured region of an articular cartilage so that a subchondral bone is exposed, and forming a cartilage edge which is nearly angled at 90° with the exposed surface of the subchondral bone to form a pool-shaped depression; forming a hole which pierces up to a cancellous bone of the subchondral bone through the depression, and scratching blood vessels in the cancellous bone; causing bleeding from the blood vessels so that blood is retained in the depression via the hole.

4 Claims, 9 Drawing Sheets

(51) Int. Cl.
     *A61B 1/00*   (2006.01)
     *A61B 1/317*  (2006.01)
     *A61B 1/04*   (2006.01)
     *A61B 1/06*   (2006.01)
(52) U.S. Cl.
     CPC .......... *A61B 1/0638* (2013.01); *A61B 1/0646* (2013.01); *A61B 1/0661* (2013.01); *A61B 1/317* (2013.01); *A61B 17/16* (2013.01); *A61B 17/1659* (2013.01); *A61B 17/320068* (2013.01)
(58) Field of Classification Search
     CPC ...... A61B 17/320016; A61B 17/32002; A61B 17/320068; A61B 17/22012; A61B 17/22; A61B 17/22004; A61B 17/22005; A61B 17/22011; A61B 17/2202; A61B 17/22021; A61B 17/22024; A61B 2017/320024; A61B 2017/320028; A61B 2017/320032
     See application file for complete search history.

(56) References Cited

U.S. PATENT DOCUMENTS

2014/0114280 A1* 4/2014 Long ................. A61L 27/24
                                                    604/506
2017/0157271 A1* 6/2017 Mizuno ............. A61K 49/0034

* cited by examiner

ARTHROENDOSCOPICAL SURGICAL METHOD

BACKGROUND OF THE INVENTION

1. Field of the Invention

The present invention relates to an arthroscopical surgical method for an arthroscopical intra-articular treatment.

2. Description of the Related Art

For example, cartilaginous tissues may be injured by external force on an articular cartilage due to sports or traffic accidents. Cartilages are tissues having poor bloodstreams, and have difficulty in self-repair once injured. Thus, a doctor (surgeon) treats the injured articular cartilage by an operation for a patient whose articular cartilage is injured.

In recent years, various treatment methods have been developed for the injury of the articular cartilage, Arthroscopical bone fenestration (a microfracture method) is minimally invasive and can be conducted at low cost. Thus, the bone fenestration is becoming the first choice to treat the articular cartilage. The bone fenestration removes a part of the articular cartilage degenerated by, for example, injuries, forms a hole in a subchondral bone, and then encourage the reproduction of the cartilage by blood and bone marrow fluid.

BRIEF SUMMARY OF THE INVENTION

One aspect of an arthroscopical surgical method using an ultrasonic treatment device for a joint includes: transmitting ultrasonic vibration to a treatment portion of the ultrasonic treatment device, removing an injured region of an articular cartilage so that a subchondral bone is exposed and formed as a bottom surface, and forming a cartilage edge which is nearly angled at 90° with the exposed surface of the subchondral bone to form a pool-shaped depression; forming a hole which pierces up to a cancellous bone of the subchondral bone through the depression, and scratching blood vessels in the cancellous bone; causing bleeding from the blood vessels so that blood is retained in the depression via the hole.

Another aspect of an arthroscopical surgical method includes: administering a fluorescent chemical agent into a joint which is a treatment target, allowing the fluorescent chemical agent to be adsorbed by a degenerated region which has degenerated from a normal region in a cartilage inside the joint which is the treatment target, displaying and observing the emission of fluorescence from the degenerated region which has adsorbed the fluorescent chemical agent by infrared excitation light on a display through an arthroscope, and allowing a surgeon to recognize the degenerated region in the cartilage inside the joint which is the treatment target.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, an embodiment of this invention will be described with reference to the drawings.

Figure 1:
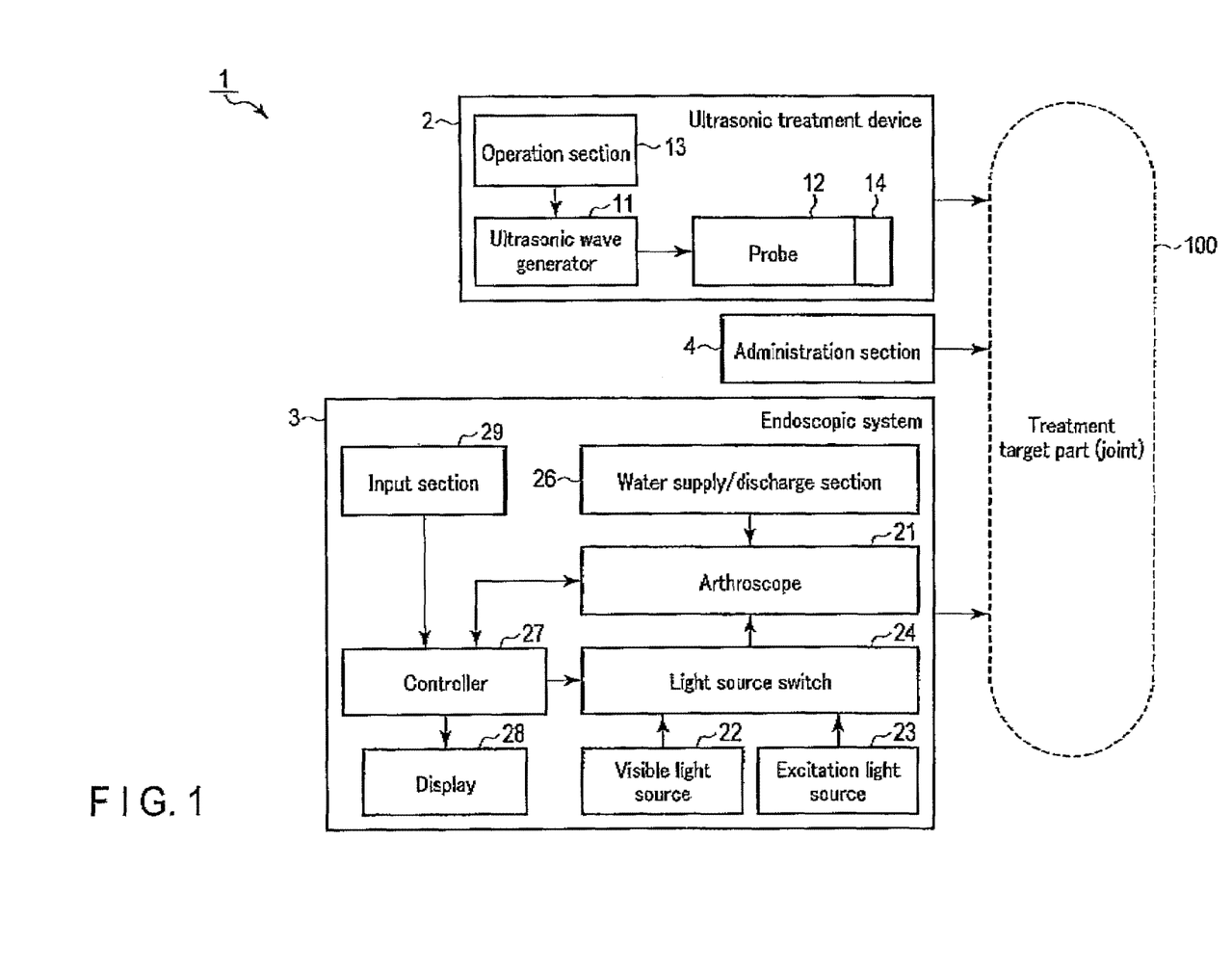
FIG. 1 is a schematic block diagram showing a surgical system according to one embodiment.

FIG. 1 shows a configuration example of a surgical system including an ultrasonic treatment device to conduct arthroscopical surgery according to the present embodiment. Although an articular cartilage 112a (see FIG. 3 and FIG. 4) of a knee joint is described as an example of a treatment target part 100 of the arthroscopical surgery in the embodiment below, the invention is also applicable to other articular cartilages such as a cubital joint.

As shown in FIG. 1, a surgical system 1 according to the present embodiment includes an ultrasonic treatment device 2, an endoscopic system 3 including an arthroscope, and an administration section 4 to administer a fluorescent chemical agent.

The ultrasonic treatment device 2 includes an ultrasonic wave generator 11 which generates ultrasonic vibration by an ultrasonic transducer (e.g. a piezoelectric element), a probe 12 which transmits the ultrasonic vibration to conduct a removal treatment of the treatment target part, and an operation section (switch) 13 which drives and controls the ultrasonic wave generator 11 and which turns on/off the generation of the ultrasonic vibration.

The probe 12 of the ultrasonic treatment device 2 is formed into the shape of an elongated metallic rod which extends along a longitudinal axis direction and which has a diameter of about 2 mm to 4 mm. The probe 12 has a distal end and a proximal end. The proximal end is coupled to the ultrasonic wave generator 11, and a treatment portion 14 is provided at the distal end. The probe 12 transmits the ultrasonic vibration generated in the ultrasonic wave generator 11 to the treatment portion 14, and brings the treatment portion 14 into contact with a degenerated region (degenerated tissue) 162 of a designated part (articular cartilage) 112a in the joint to conduct a cutting treatment. This treatment portion 14 is formed into a suitable shape such as a rasp shape or a hook shape. More than one treatment portion 14 that is bent at any different angles ranging from, for example, 10 to 30 degrees with the longitudinal axis direction of the probe 12 may be prepared. A probe having a suitable angle is properly selected in accordance with the contents of a treatment for the treatment target part 100 and the positional relation between the portal to insert the treatment portion 14 and a treatment part. The rasp-type treatment portion 14 shown in FIG. 6 includes a treatment surface 14a having protrusions and a file-finished projecting surface. The ultrasonic treatment device 2 having the rasp-type treatment portion 14 can be used, for example, to smooth tissues and cut synovial membranes.

This ultrasonic treatment device 2 brings the treatment portion 14 provided at the distal end of the probe 12 to which the ultrasonic vibration is transmitted into contact with a treatment target part such as a cartilage to mechanically cut by micro sliding actions. The ultrasonic treatment device 2 can adjust the amount of cutting by adjustment of amplitude and/or the degree at which the treatment portion 14 is pressed to the treatment target part.

This ultrasonic treatment device 2 can adjust the amount of cutting (the depth of cutting) by the degree of strength of pressing the distal treatment portion 14 to the treatment part owing to the mechanical cutting by micro sliding actions in which the ultrasonic vibration is applied to the probe 12 having one end supported by the ultrasonic wave generator 11. That is, if the treatment portion 14 is brought into light contact with the treatment target part, the surface of the treatment target part is smoothed or minutely cut with a small amount of cutting of the treatment target part. In contrast, if the treatment portion 14 is brought into heavy contact with the treatment target part, the surface of the treatment target part is smoothed or minutely cut with a great amount of cutting of the treatment target part. Thus, the amount of cutting (the depth of cutting) of the treatment target part is adjusted in accordance with force adjustment by a surgeon, and effective resection is achieved.

The endoscopic system 3 includes an arthroscope 21 including a rigid endoscope which is a kind of endoscope. As illumination light sources, the endoscopic system 3 includes a visible light source 22 which emits visible light (white light), and an excitation light source 23 which emits excitation light that will be described later. The endoscopic system 3 also includes a light source switch 24 which switches the light to exit from the arthroscope 21 between the visible light and the excitation light, a water supply/discharge section 26 which causes a perfusion fluid for joint surgery to be supplied to, discharged from, or perfused in the periphery including the treatment target part 100, a controller 27 which controls the overall endoscopic system 3, a display 28 which displays observation information including images obtained by the arthroscope 21 and also displays surgical information including imaged surgical conditions, and an input section 29 such as a keyboard or a touch panel. Although the water supply/discharge section 26 causes the perfusion fluid for joint surgery to be supplied to or discharged from the treatment part through the arthroscope 21 in the present embodiment, the perfusion fluid for joint surgery may be supplied to or discharged from the ultrasonic treatment device 2.

In the present embodiment, bloodstreams, for example, are visualized by the use of fluorescence under an infrared (IR) observation when the treatment target part 100 is treated. Here, blood vessels and bloodstream information are highlighted by the administration of indocyanine green (ICG) which is a fluorescent chemical agent that easily absorbs infrared light and by the use of infrared light having high transmissivity. The administration section 4 shown in FIG. 1 intravenously and/or directly administers the fluorescent chemical agent ICG into the joint 100. The administration section 4 is known and is therefore not described in detail.

Fluorescent display by the fluorescent chemical agent ICG is highly reliable in living bodies, and is used in, for example, a liver function test, a circulatory function test, and cerebral angiography, and is not chemically changed in the bodies. The fluorescent chemical agent ICG shows an exponential decrease in the change of its concentration in plasma up to about 15 minutes after administration of the fluorescent chemical agent ICG, and then shows a slow decrease and rapidly disappears from blood plasma.

Figure 2:
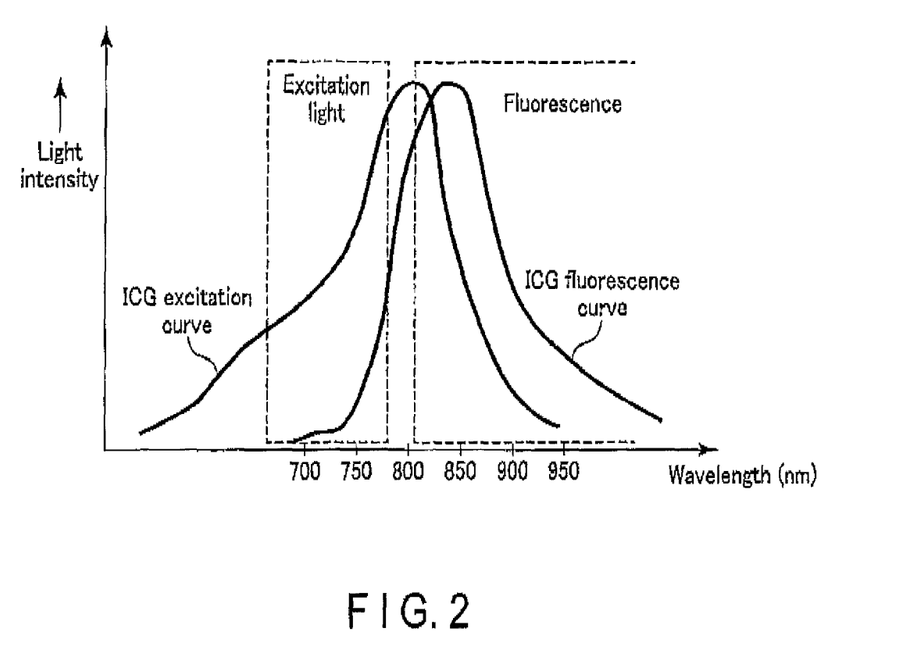
FIG. 2 is a schematic diagram showing an example of the relation between excitation light to conduct an IR observation using the surgical system according to one embodiment and fluorescence which is emitted due to the influence of the excitation light and which is longer in wavelength than the excitation light.

It excited by the irradiation of, for example, near infrared excitation light having a wavelength of 670 to 790 nm (ICG excitation curve), the fluorescent chemical agent ICG emits near infrared (ICG fluorescence curve) fluorescence which is longer in wavelength than the excitation light and which has a peak wavelength of, for example, 835 nm, as shown in known characteristics in FIG. 2. Bloodstreams in deep parts (about 2 to 3 mm from the surface) of a living body can be observed by the emission of the fluorescence. However, the emission of the fluorescence by the fluorescent chemical agent ICG is not directly visible to the naked eye of a human being, Thus, if an image pickup device (e.g. a CCD or a CMOS) capable of imaging an object at the above wavelength band is used in the arthroscope 21, the surgeon can observe the state inside the joint 100 by a normal light observation and the state inside the joint 100 by an IR observation using the excitation light as images displayed on the display 28.

Figure 5A:
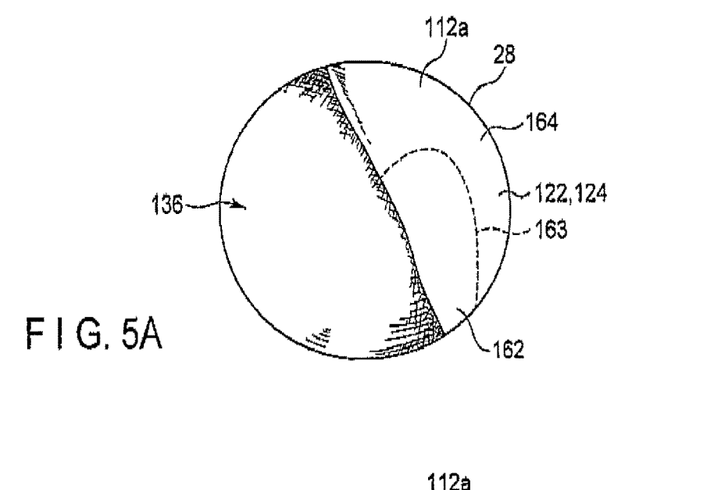
FIG. 5A is a schematic diagram of a display showing how the inside of an articular cavity is observed through the arthroscope using a visible light source.
Figure 5B:
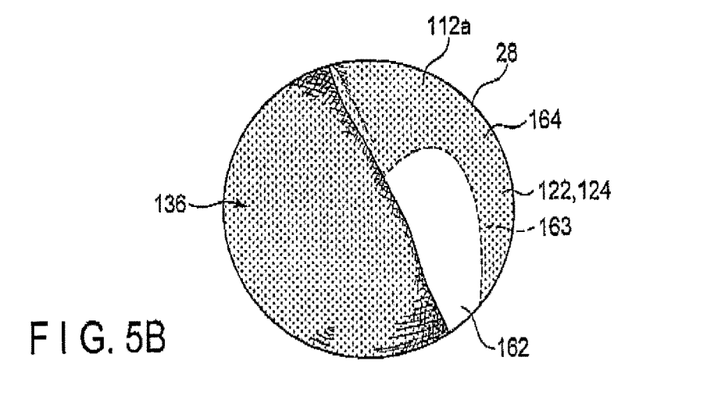
FIG. 5B is a schematic diagram of the display showing how an excitation light source is used to emit fluorescence to highlight a degenerated region in the articular cavity relative to normal regions through the arthroscope with a fluorescent chemical agent attached to the degenerated region.

As shown in FIG. 5A and FIG. 5B, the endoscopic system 3 has a configuration in which the light sources 22 and 23 can be switched by the light source switch 24 in the present embodiment, and can observe the same observation target while switching to the visible light (see FIG. 5A) for use in a normal observation or the infrared light (see FIG. 5B) during the observation. The degenerated region is identified in comparison with the normal region by switching to a first observation mode in which fluorescence is emitted by irradiation of infrared excitation light and the fluorescence in the degenerated region is displayed on the display 28 through the arthroscope 21 and observed, and a second observation mode in which white light is irradiated and the normal region and the degenerated region in the joint 100 is displayed on the display 28 through the arthroscope 21 and observed. A changeover switch of the light sources 22 and 23 may be provided in the arthroscope 21 or may be provided separately from the arthroscope 21. Moreover, in the present embodiment, the touch panel is used as the input section 29 on the surface of the display 28 to provide a known function that enables lines to be drawn on a screen of the display 28 by the input with a fingertip or the touch of a pen or by cursor movement using a mouse. For example, when the surgeon is observing a part in the joint 100 that is emitting fluorescence with the fluorescent chemical agent ICG on the screen of the display 28, the surgeon or an assistant traces on the screen with the fingertip to differentiate a particular region that is emitting fluorescence. In this instance, a line is drawn on the trace. If the light source switch 24 is switched to set a normal light observation mode while the line drawn on the screen by the surgeon is maintained, a line is drawn on the display screen of the display 28. If this line is used as a cutting line to cut with the treatment portion 14 of the ultrasonic treatment device 2, a region to be chipped can be easily determined.

Figure 3:
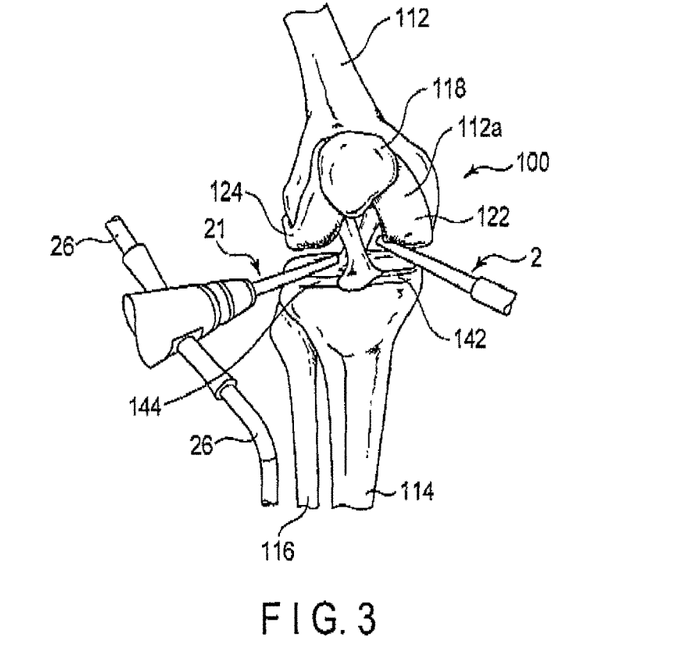
FIG. 3 is a schematic diagram showing how an arthroscope and a treatment portion of an ultrasonic treatment device are respectively inserted into an articular capsule of a knee joint of a right knee from different portals when seen from the front.
Figure 4:
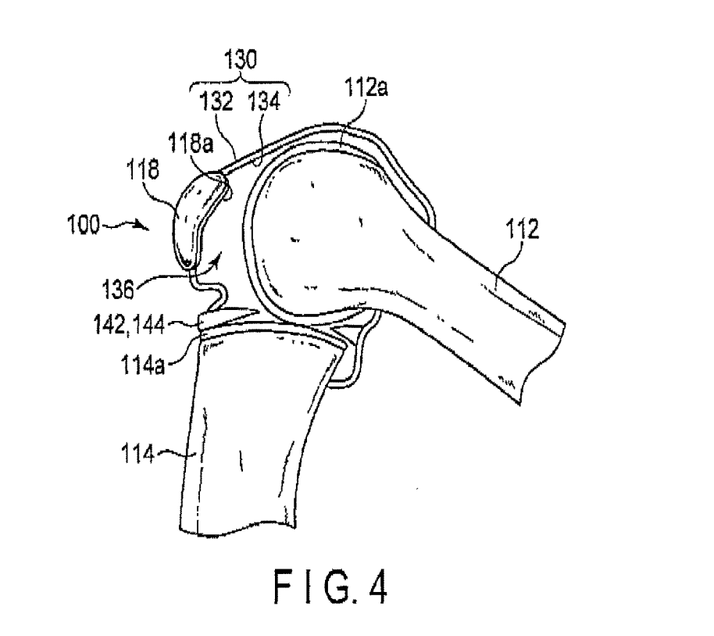
FIG. 4 is a schematic side view showing the knee joint of the right knee wrapped in the joint capsule when seen from the inside.

Now, a right knee is described by way of example. As shown in FIG. 3, the knee joint 100 mainly includes a femur 112, a tibia 114, a fibula 116, and a patella 118. As shown in FIG. 4, the knee joint 100 is wrapped in a joint capsule 130. The joint capsule 130 includes a fibrous tunica 132 outside and a synovial membrane 134 inside. The synovial membrane 134 forms folds and secretes a joint fluid for smooth movement of the knee joint 100. The inside of the joint capsule 130 is referred to as an articular cavity 136. The articular cavity 136 is filled with the joint fluid secreted from the synovial membrane 134.

In the knee joint 100, cartilages (articular cartilages) 112a, 114a, and 118a are present between bones (the femur 112, the tibia 114, and the patella 118). The cartilages 112a, 114a, and 118a absorb an impact in the knee joint 100, and enable smooth movement of the knee joint 100.

As shown in FIG. 3, surfaces of the femur 112 joined to the tibia 114 are referred to as a medial condyle 122 and a lateral condyle 124, respectively. The upper surface of the tibia 114 has two surfaces that are joined to the medial condyle 122 and the lateral condyle 124 of the femur 112. Menisci 142 and 144 and ligaments 152 and 154 are attached between the medial condyle 122 and the lateral condyle 124 of the femur 112 and the upper surface of the tibia 114.

The menisci 142 and 144 make a pair inside and outside. The upper surface of the medial meniscus 142 extends along the spherical cartilage 112a disposed in the medial condyle 122 of the femur 112, and the lower surface of the medial meniscus 142 extends along the flat cartilage 114a disposed on the upper surface of the tibia 114. Similarly, the upper surface of the lateral meniscus 144 extends along the spherical cartilage 112a disposed in the lateral condyle 124 of the femur 112, and the lower surface of the lateral meniscus 144 extends along the flat cartilage 114a disposed on the upper surface of the tibia 114. The menisci 142 and 144 have thick outer edges and thin inner edges. The outer edges of the medial meniscus 142 and the lateral meniscus 144 are continuous with the joint capsule 130.

The knee joint 100 has an anterior cruciate ligament 152 and a posterior cruciate ligament 154. When the knee joint 100 is Seen from the front, the anterior cruciate ligament 152 is located in front, and the posterior cruciate ligament 154 is located in the rear. One end of the anterior cruciate ligament 152 is fixed to its rear through the space between the medial condyle 122 and the lateral condyle 124 of the femur 112, and the other end of the anterior cruciate ligament 152 is fixed to the front of the upper surface of the tibia 114.

An example of how the surgical system 1 according to the present embodiment is used to implement bone fenestration (a microfracture method) to encourage the reproduction of a degenerated region/injured region of the cartilage for a patient having, for example, the injured articular cartilage 112a of the right knee, that is, an arthroscopical surgical method is described. According to this procedure, the surface of a subchondral bone exposed by dissection of the degenerated region/injured region of the cartilage is fenestrated to guide blood and bone marrow fluid into the dissected part of the cartilage and accelerate repair in a fibrous cartilage. This procedure is known to be relatively simple and convenient, but needs to be conducted with certainty to expect a satisfactory tissue repair.

In the example described here, the doctor (surgeon) uses the surgical system 1 described above to treat the degenerated region/injured region of the cartilage 112a under the arthroscope 21 for the patient having the degenerated region/injured region in the cartilage 112a, Treatments of inflammation and others in the synovial membrane 134 inside the joint capsule 130 of the knee joint 100 are not described.

The surgeon makes about two or three portals (not shown) in the circumference (skin surface) of the joint 100 while properly bending the right knee of the patient. For example, in the explanation here, the arthroscope (rigid endoscope) 21 is inserted from the outside portal, and various treatment devices (curing devices) are inserted from the inside portal. Naturally, the various treatment devices (curing devices) may be inserted into articular cavity 136 from the outside portal, and the arthroscope 21 may be inserted into the articular cavity 136 from the inside portal to conduct a treatment. When the arthroscope (rigid endoscope) 21 is inserted into the articular cavity 136 of the joint 100 from the outside portal, the visible light source 22 is selected as the light source, and the normal light observation mode is set.

As shown in FIG. 5A, while the articular cavity 136 is filled with the perfusion fluid for joint surgery by the arthroscope 21, the surgeon properly moves the arthroscope 21 checking images shown on the display 28 of the arthroscope 21 so that the treatment target part is shown in the screen of the display 28. This surgeon advances the treatment while observing the treatment target part through the arthroscope 21. The perfusion fluid for joint surgery is perfused in the articular cavity 136 by the use of the arthroscope 21.

The fluorescent chemical agent ICG is administered to the vein of the patient by using the administration section 4. After the elapse of a proper time, the light source of the arthroscope 21 is switched to the excitation light source 23 from the visible light source 22, that is, the observation form is switched to the infrared (IR) observation mode from the normal light observation mode. In this instance, the fluorescent chemical agent ICG is excited, and fluorescence is emitted. If the fluorescent chemical agent ICG is contained in the bloodstreams at the observation position, fluorescence is emitted. The emitted fluorescence is displayed on the display 28 through the arthroscope 21, That is, the fluorescent chemical agent ICG is administered to the vein of the patient so that the fluorescent chemical agent ICG is contained in the blood, and the fluorescence in the fluorescent chemical agent ICG is emitted by infrared excitation light to display and observe blood vessels in the joint 100 and bloodstream information on the display through the arthroscope 21.

The surgeon switches the light source of the arthroscope 21 to the visible light source 22. The size and depth of the degenerated region (injured region) 162 in the articular cartilage 112a and the hardness of the cartilage are checked by the observation (normal light observation) using the visible light source 22 in the joint 100 through the arthroscope 21. There may be more than one degenerated region or injured region instead of one degenerated region or injured region. Here, it may be difficult to check the degenerated region 162 in the cartilage 112a by the visible light source 22. The cartilage 112a is poor in bloodstreams, so that even if the light source of the arthroscope 21 is switched to the excitation light source 23 from the visible light source 22, it can be difficult to check the position of the degenerated region 162 in the cartilage 112a.

In addition to the fluorescent chemical agent ICG administered to the vein of the patient, the fluorescent chemical agent ICG is also directly administered into the joint 100 of the right knee by the use of the administration section 4. Preferably, the fluorescent chemical agent ICG is directly administered to the position of the cartilage 112a where the position is estimated to be the degenerated region 162.

In this case, the fluorescent chemical agent ICG is inherently adsorbed by the tissue of the degenerated region 162 in the cartilage 112a, Thus, the light Source switch 24 of the endoscopic system 3 is operated to switch the light source of the arthroscope 21 to the excitation light source 23 from the visible light source 22. In this instance, the display 28 is changed to the state shown in FIG. 5B from the state shown in FIG. 5A. In FIG. 5B, the emitted fluorescence, that is, the degenerated region 162 is displayed brightly and a normal region (normal tissue) 164 is displayed darkly in the display 28, Thus, the surgeon can recognize the degenerated region 162 in the cartilage 112a. The region other than the region where the fluorescence is emitted is estimated to be the normal region 164.

Before removing the tissue of the degenerated region 162 in the articular cartilage 112a, the surgeon properly operates the light source switch 24 to recognize a boundary 163 between the degenerated region 162 and the normal region 164. That is, by administering the fluorescent chemical agent ICG into the joint 100 which is the treatment target, the surgeon allows the fluorescent chemical agent ICG to be adsorbed by the degenerated region 162 in the cartilage 112a inside the joint 100 which is the treatment target, displays and observes the emission of fluorescence from the degenerated region 162 which has adsorbed the fluorescent chemical agent ICG by the infrared excitation light on the display 28 through the arthroscope 21, and specifies the degenerated region 162 in the cartilage 112a inside the joint 100 which is the treatment target.

The surgeon then evaluates the changes of the intake of the fluorescent chemical agent ICG into the normal region 164 and the degenerated region 162 in the articular cartilage 112a and the excretion thereof by the IR observation using the arthroscope 21. In the IR observation, the degenerated region 162 can be specified up to a depth of about 2 mm to 3 mm. Thus, the surgeon can three-dimensionally specify the degenerated region 162 by the IR observation using the fluorescent chemical agent ICG. In the normal light observation through the arthroscope 21, it may be difficult to recognize the injured region. It is possible for the surgeon to accurately recognize the normal region 164/the injured region 162 in the articular cartilage by combining the IR observation using the fluorescent chemical agent ICG with the normal light observation. In this instance, the input section 29 which is, for example, a touch panel or a PC mouse may be used to mark a region (the degenerated region 162) to be cut. In this case, the surgeon can easily recognize the region to be cut even in the normal light observation by maintaining the marking in the display on the display 28.

Figure 6:
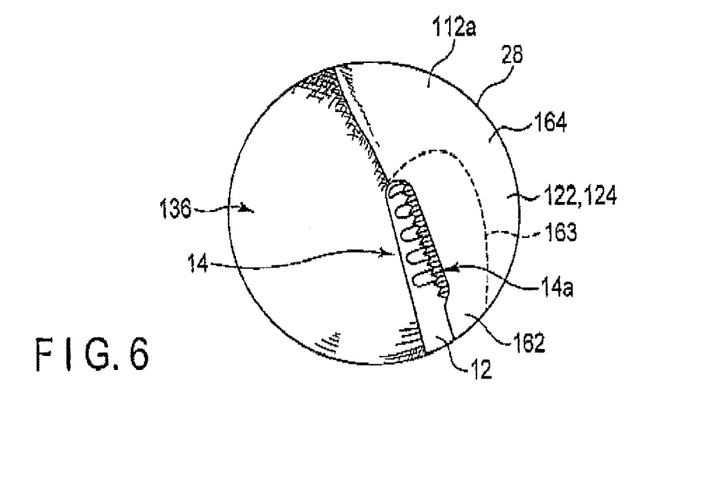
FIG. 6 is a schematic diagram of the display showing how a treatment surface of the treatment portion of the ultrasonic treatment device which has passed through the portal is brought into abutment with the degenerated region while the inside of the articular cavity is being observed through the arthroscope using the visible light source.

When the surgeon recognizes by the IR observation using the arthroscope 21 that the degenerated region 162 is present in the cartilage 112a, the surgeon inserts the treatment portion 14 of the ultrasonic treatment device 2 having the suitable treatment portion 14 into the articular cavity 136 from the inside portal. In the example described here, the treatment portion 14 is a rasp-type. As shown in FIG. 6, while observing the inside of the articular cavity 136 in the white light (normal light) observation mode of the arthroscope 21, the surgeon brings the treatment surface 14a of the treatment portion 14 into contact with the degenerated region 162 in the articular cartilage 112a to conduct a cutting treatment simultaneously with the generation of ultrasonic vibration by the ultrasonic treatment device 2.

When the size and depth of the degenerated region 162 in the articular cartilage 112a and the hardness of the cartilage are checked, a steel device such as a cupped forceps or a sharp curette (not shown) has heretofore been used. The size and depth of the degenerated region 162 and the hardness of the cartilage can be checked by the use of the treatment portion 14 of the ultrasonic treatment device 2 that is not generating ultrasonic vibration instead of the above devices. Since the treatment portion 14 of the ultrasonic treatment device 2 is made of a rigid material such as a titanium alloy material, the hardness of the cartilage can be checked as in the case in which the above devices are used.

While always observing the treatment target part in the field of view through the arthroscope 21, the surgeon then operates the operation section 13 of the ultrasonic treatment device 2 to generate ultrasonic vibration in the ultrasonic wave generator 11, and transmits the ultrasonic vibration to the treatment portion 14 of the ultrasonic treatment device 2 through the probe 12. The surgeon then removes the degenerated region 162 in the cartilage 112a with the treatment surface 14a of the treatment portion 14 to expose a surface 166a of a subchondral bone (here, the medial condyle 122 or the lateral condyle 124 of the femur 112) 166 (see FIG. 7A to FIG. 8B). Here, the degenerated region 162 alone is resected, and the normal region 164 is resected to the minimum. The generation of the ultrasonic vibration is temporarily stopped when the removal of the degenerated region 162 has advanced to some degree.

Figure 7A:
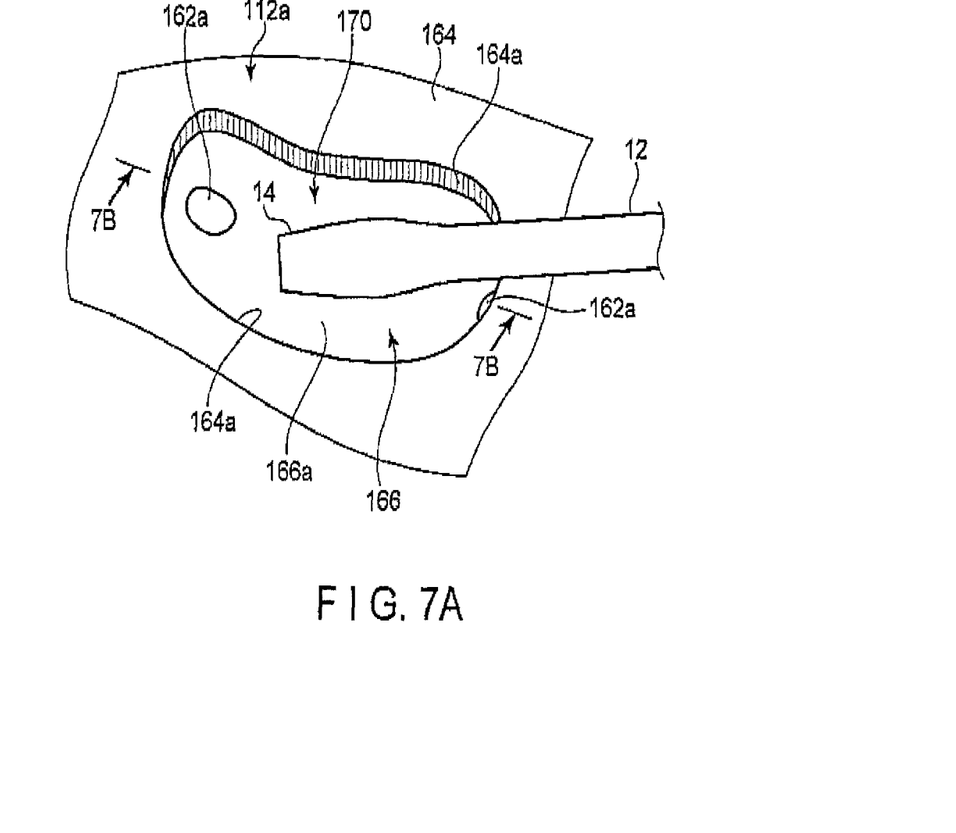
FIG. 7A is a schematic diagram showing a process in which ultrasonic vibration is transmitted to the treatment portion of the ultrasonic treatment device to remove the degenerated region by the treatment surface of the treatment portion and expose a subchondral bone.
Figure 7B:
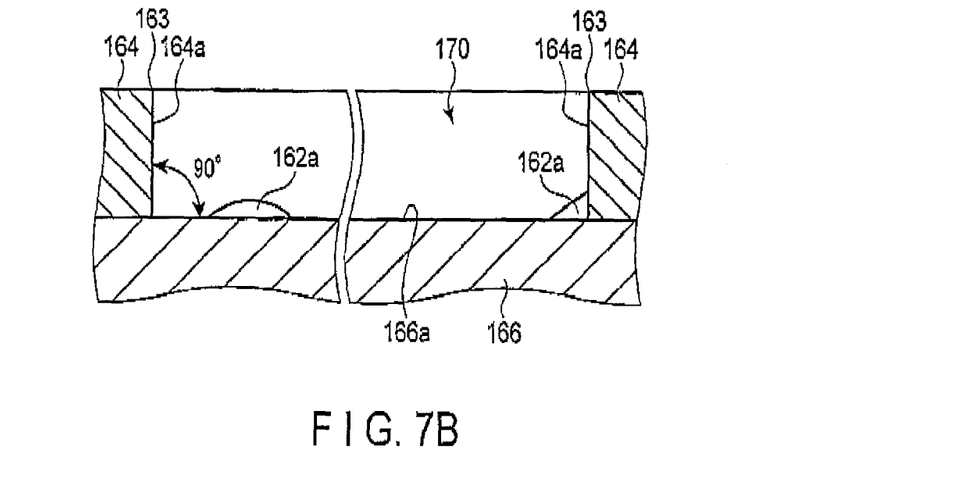
FIG. 7B is a schematic sectional view taken along the line 7B-7B in FIG. 7A.

If unstable pieces of the cartilage remain in the joint 100 which is the treatment target, remaining pain or dropsy may affect the postoperative results. The surgeon needs to completely remove unstable pieces of the cartilage such as the degenerated region in the cartilage 112a. Therefore, it is necessary to carefully check whether there is any residual of the degenerated region 162. After the resection of the degenerated region 162, the surgeon operates the light source switch 24 to switch to the excitation light source 23 from the visible light source 22, and checks a remaining amount (residual) 162a of the degenerated region 162 in the cartilage 112a. The fluorescent chemical agent ICG is adhering to the residual 162a as a part of the degenerated region 162. Thus, as shown in FIG. 5B, the emitted fluorescence, that is, the degenerated region 162 is displayed brightly and the normal region 164 is displayed darkly in the display 28. Therefore, the surgeon can easily check the residual 162a by the IR observation. As shown in FIG. 7A to FIG. 7B, when the residual 162a is present, the surgeon again operates the light source switch 24 to switch to the visible light source 22 from the excitation light source 23, and then transmits ultrasonic vibration to the treatment portion 14 of the ultrasonic treatment device 2 and resects the residual 162a. In this way, the surgeon properly dissects the cartilage 112a with the treatment surface 14a by moving the treatment portion 14 while transmitting the ultrasonic vibration to the treatment portion 14 of the ultrasonic treatment device 2.

Figure 8A:
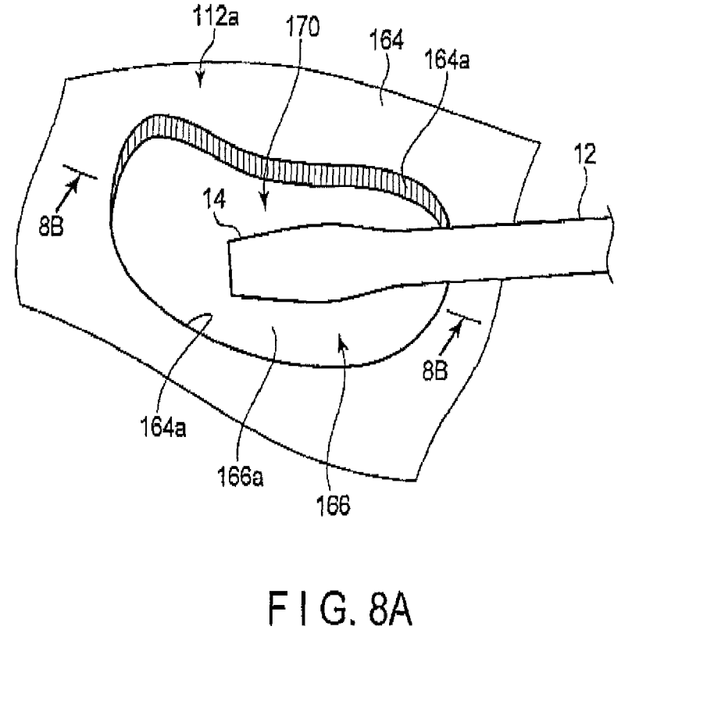
FIG. 8A is a schematic diagram showing how the ultrasonic vibration is transmitted to the treatment portion of the ultrasonic treatment device, the degenerated region has been removed by the treatment portion so that the removal of the degenerated region by the treatment surface of the treatment portion is finished and the subchondral bone is exposed.
Figure 8B:
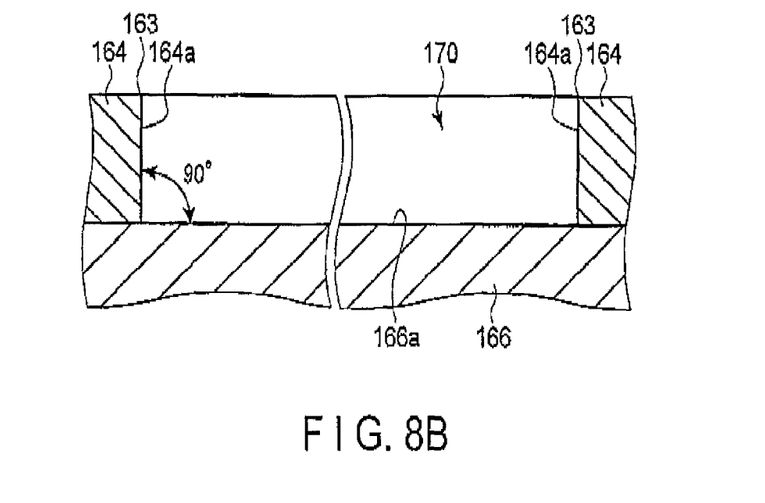
FIG. 8B is a schematic sectional view taken along the line 8B-8B in FIG. 8A.

In this instance, as shown in FIG. 8A and FIG. 8B, the degenerated region 162 is dissected up to the boundary 163 between the degenerated region 162 and the normal region 164 of the cartilage 112a as described above. When the degenerated region 162 is resected, a pool-shaped depression 170 in which the surface 166a of the subchondral bone 166 is the bottom surface (exposed surface) and in which the normal region 164 of the cartilage 112a is an edge (bank) 164a is formed. The depression 170 is formed by the treatment with the ultrasonic treatment device 2 using the ultrasonic vibration so that the angle (bank angle) between the surface 166a of the subchondral bone 166 and the edge 164a of the normal region 164 is about 90°.

In this way, the ultrasonic vibration is transmitted to the treatment portion 14 of the ultrasonic treatment device 2 to remove the degenerated region 162 in the articular cartilage 112a so that the subchondral bone 166 is exposed and formed as the bottom surface 166a, and the cartilage edge 164a which is nearly angled at 90° with the exposed surface 166a of the subchondral bone 166 is formed to form the depression 170. After having created the depression 170, the surgeon switches the light source switch 24 of the arthroscope 21 to the excitation light source 23 to observe by infrared light whether there is any residual of the degenerated region 162 of the cartilage 112a. When there is a residual, the surgeon uses the visible light source 22 to transmit the ultrasonic vibration to the treatment portion 14 of the ultrasonic treatment device 2 to remove the residual.

By switching the light source switch 24 to the excitation light source 23, the surgeon can specify a calcified region (not shown) of the cartilage 112a as well as the degenerated region (injured region) 162 in the articular cartilage 112a. The calcified region is removed by the treatment portion 14 of the ultrasonic treatment device 2 to which the ultrasonic vibration is transmitted as in the case of the degenerated region 162. In this case as well, the calcified region alone is cut, and the normal region 164 is resected to the minimum. When the calcified region is resected, the depression 170 in which the surface 166a of the subchondral bone 166 is the bottom surface and in which the normal region 164 of the cartilage 112a is the edge (bank) 164a is formed.

The surgeon switches the light source switch 24 to the excitation light source 23, checks by the IR observation that the degenerated region 162 and the calcified region that need to be treated have been totally removed, and then pulls the ultrasonic treatment device 2 having the treatment portion 14 out of the inside portal.

When the treatment using the ultrasonic treatment device 2 is conducted, the ultrasonic treatment device 2 does not need to be pulled out of the inside portal even if more than one degenerated region 162 are present, and the same ultrasonic treatment device 2 can be used to advance the treatment.

Figure 9A:
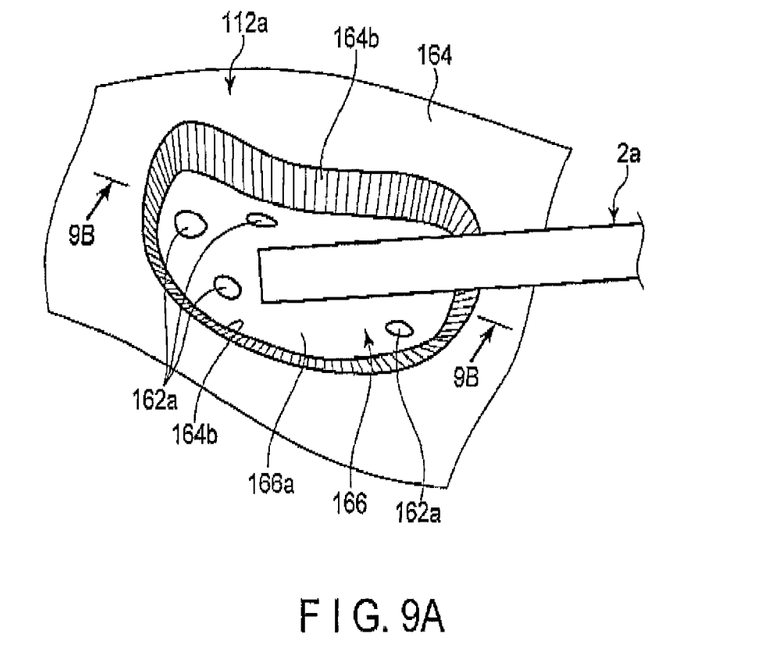
FIG. 9A is a schematic diagram showing how the degenerated region has been removed by a treatment portion of an device which is not the ultrasonic treatment device through the portal.
Figure 9B:
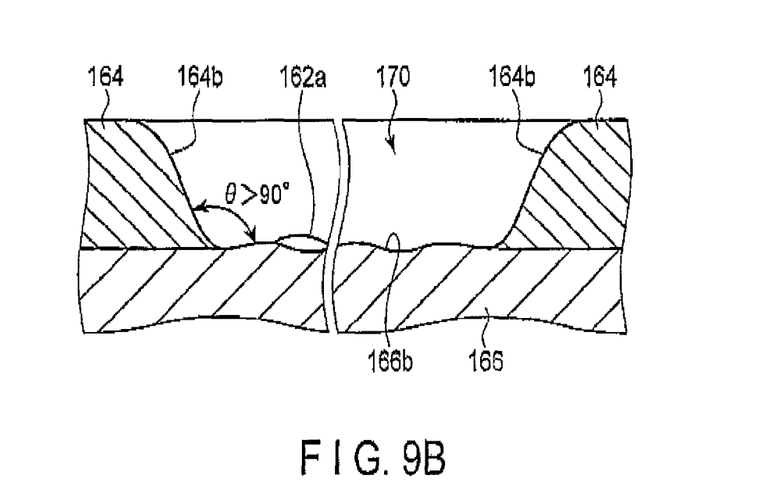
FIG. 9B is a schematic sectional view taken along the line 9B-9B in FIG. 9A.

Here, when the ultrasonic treatment device 2 is not used but a steel device 2a (see FIG. 9A) such as sharp curette is used, it is difficult to totally remove the degenerated region 162 even if an attempt to remove the degenerated region 162 is made, and the residual 162a shown in FIG. 9A and FIG. 9B tends to remain. When the steel device 24, for example, the sharp curette is used, the treated surface (exposed surface) tends to be formed as a depressed/protruding surface 166b. If, for example, a shaver (not shown) is used, a cutting range increases more than necessary, and invasion tends to expand to the normal region 164. When the ultrasonic treatment device 2 is used, a necessary range of the cartilage 112a alone can be resected into a necessary state. If the steel device 2a, for example, the sharp curette or the shaver is used, the angle between the exposed surface 166b of the subchondral bone 166 of the depression 170 and an edge 164b of the normal region 164 is more likely to be more than 90°, as shown in FIG. 9A and FIG. 9B.

Figure 10A:
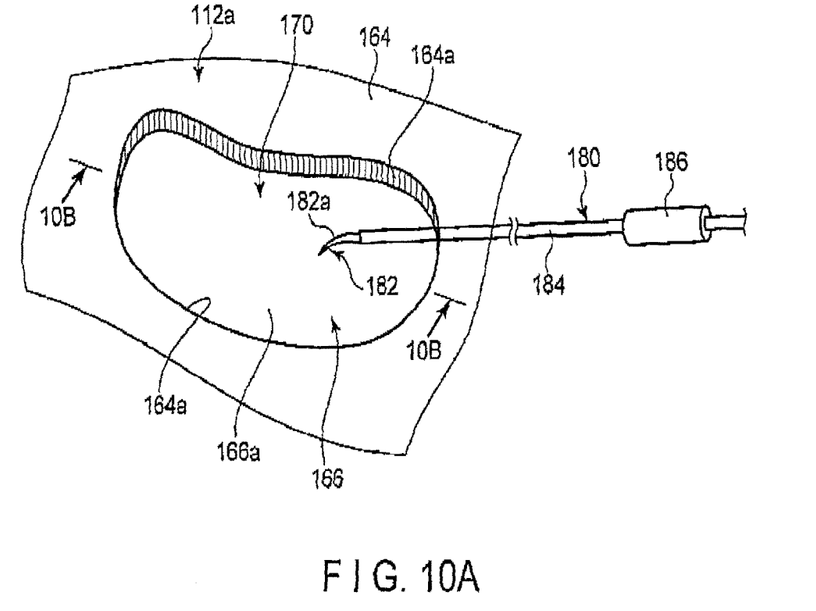
FIG. 10A is a schematic diagram showing how a hole is formed in the exposed surface of the subchondral bone by an ultrasonic pick through the portal.

A boring portion 182a of an ultrasonic pick (another ultrasonic treatment device) 180 shown in FIG. 10A is inserted into the inside portal from which the ultrasonic treatment device 2 has been removed. The ultrasonic pick 180 shown in FIG. 10A has the boring portion 182a at the distal end of a probe 182 which has a suitable length and which is made of a titanium alloy material and to which ultrasonic vibration is transmitted. The outside of the probe 182 is covered with an electrically insulating sheath 184. An ultrasonic vibrator 186 which generates ultrasonic vibration having a suitable frequency and amplitude is fixed to the proximal end of the probe 182. The part of the probe 182 covered with the sheath 184 is formed straight or substantially straight in consideration of the efficiency of approaching a part to be bored. The boring portion 182a is bent so that its distal end abuts on the exposed surface 166a of the subchondral bone 166 of the depression 170.

The surgeon switches the light source switch 24 to the visible light source 22, and brings the boring portion 182a of the ultrasonic pick 180 into abutment with the exposed surface 166a of the subchondral bone 166 while checking the observation screen of the display 28 in which the arthroscope 21 is set to the visible light observation mode.

Figure 10B:
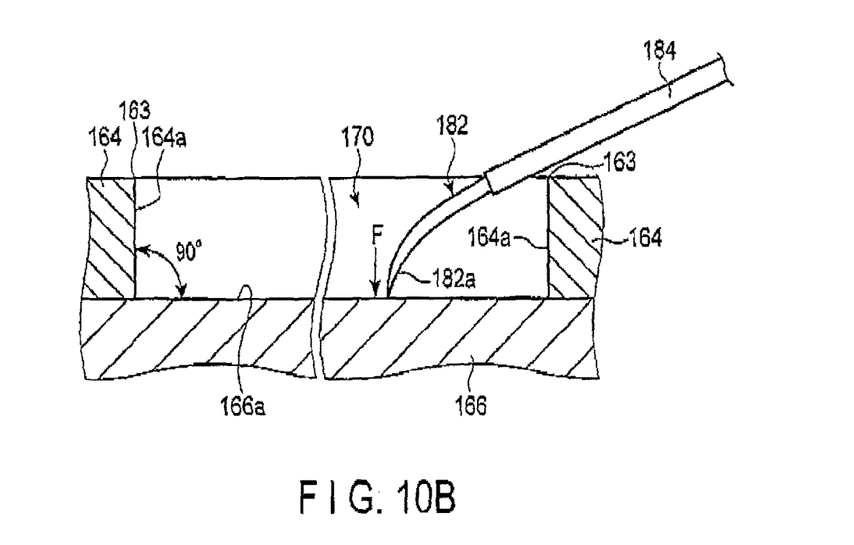
FIG. 10B is a schematic sectional view taken along the line 10B-10B in FIG. 10A showing how a boring portion (treatment portion) of the ultrasonic pick is brought into abutment with the exposed surface of the subchondral bone.
Figure 10C:
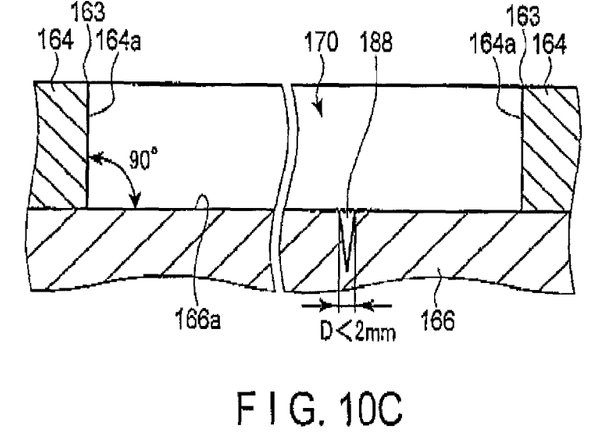
FIG. 10C is a schematic sectional view taken along the line 10B-10B in FIG. 10A showing how a hole having a diameter D smaller than 2 mm is formed in the exposed surface of the subchondral bone by the boring portion of the ultrasonic pick.

Ultrasonic vibration having a suitable frequency and amplitude is generated in the ultrasonic vibrator 186 (see FIG. 10A), and the ultrasonic vibration is transmitted to the boring portion 182a at the distal end of the probe 182 from its proximal end. As shown in FIG. 10B, the boring portion 182a is pressed in the direction of an arrow F. As shown in FIG. 10C, a hole 188 is formed in the exposed surface 166a of the subchondral bone 166 by the boring portion 182 of the ultrasonic pick 180. When the ultrasonic vibration is used to form the hole 188, the direction in which the hole 188 is made can be the same as the direction (the direction of the arrow F) in which the boring portion (treatment portion) 182a is pressed. It is therefore possible to prevent the hole 188 in an unintended direction (a direction different from a desired direction) from being made in the exposed surface 166a of the subchondral bone 166.

When the ultrasonic vibration is used to form the hole 188 in this way, invasion of heat in the exposed surface 166a of the subchondral bone 166 can be reduced. When the ultrasonic vibration is used, it is also possible to form the desired hole 188 without breaking the exposed surface 166a of the subchondral bone 166.

The boring portion 182a of the ultrasonic pick 180 preferably forms the hole 188 which has a diameter D smaller than 2 mm and which pierces up to a cancellous bone. Thus, the boring portion 182a of the ultrasonic pick 180 according to the present embodiment has an outside diameter less than 2 mm so that the hole 188 smaller than 2 mm can be formed. This is because it has been increasingly evident that the postoperative treatment results are better if the diameter of the hole 188 is smaller, for example, about 1 mm. Actually, such a hole 188 having a proper diameter of less than 2 mm can be formed by the use of the ultrasonic pick 180 using ultrasonic vibration. A conventional device (known pick or electric pick) generally forms the hole 188 of about 2 mm.

The surgeon preferably causes the boring portion 182a to which ultrasonic vibration is transmitted to fenestrate the exposed surface (surface) 166a of the subchondral bone 166 until the hole 188 has a depth of about 15 mm. In this case, the hole 188 generally reaches the cancellous bone relative to the exposed surface (surface) 166a of the subchondral bone 166. It is therefore possible to scratch blood vessels in the cancellous bone and cause bleeding from the damaged part, Bleeding from the blood vessels is then caused so that blood is retained in the depression 170 via the hole 188. A density of about 10 holes 188 per square centimeter is preferable.

The light source switch 24 is switched to the excitation light source 23 as needed, and the bleeding is checked through the hole 188 in the IR observation mode of the arthroscope 21. Even if the surgeon cannot check the bleeding in the normal observation mode of the visible light source 22 of the arthroscope 21, the surgeon can recognize the position of the blood relative to the depression 170 by the IR observation using the excitation light source 23 based on the fluorescent chemical agent ICG which has been administered to the vein, and check whether the blood exudes into the depression 170 through the hole 188 formed by the ultrasonic pick 180. That is, bloodstreams in deep parts (about 2 to 3 mm from the surface) of a living body can be observed in the IR observation mode. Thus, bleeding has only to be checked in the IR observation mode even though bleeding cannot be checked in the normal light observation mode.

More blood and bone marrow fluid are retained in the depression 170 by the cartilage edge 164a which is nearly angled at 90° with the exposed surface 166a of the subchondral bone 166 so that the reproduction of the tissues of the cartilage is accelerated.

In the example described here, the ultrasonic pick 180 is used to form the hole 188, Although heat can invade the subchondral bone 166, an electric pick or the like may be used to form the hole 188. The proximal end of a known pick (a pick which does not use ultrasonic vibration) may be hit to form a hole by the distal end of the pick. In this case, the pick might slide on the exposed surface 166a of the subchondral bone 166 along the longitudinal direction without forming a hole by the distal end. In this case, a hole in a wrong direction might be formed in the subchondral bone 166. Otherwise, a suitable wire may be used instead of the ultrasonic pick 180 to form the hole 188.

Although the cartilage 112a of the femur 112 is treated in the example described here, the lower cartilage 118a (see FIG. 4) of the patella 118 can also be treated in a similar manner. Although the right knee has been described by way of example in this embodiment, similar bone fenestration (microfracture method) can be implemented for, for example, the cartilage of the cubital joint or the ankle joint.

As described above, the following can be said according to the procedure of removing the degenerated region 162 in the cartilage 112a under the arthroscope 21.

When the degenerated region 162 in the cartilage 112a is treated, the fluorescent chemical agent ICG is used and administered into the joint 100 in particular, and the normal light observation and the IR observation are used together so that the degenerated region 162 can be more easily recognized. The treatment surface 14a of the treatment portion 14 to which ultrasonic vibration is transmitted is used in the treatment so that the exposed surface 166a of the subchondral bone 166, for example, the medial condyle 122 of the femur 112 can be easily exposed, and the degenerated region 162 can be resected with certainty.

Furthermore, when the ultrasonic pick 180 is used to form the hole 188 in the exposed surface 166a of the subchondral bone 166 as well, the IR observation is used together if bloodstreams cannot be recognized in the normal observation, so that repeated load of the ultrasonic pick 180 on the exposed surface 166a of the subchondral bone 166 can be inhibited.

The depression 170 permits the angle (bank angle) between the exposed surface 166a of the subchondral bone 166 and the edge 164a of the normal region 164 to be about 90° (see FIG. 8B). Thus, the amount of the liquid exuding from the bone marrow that can be retained in the depression 170 can be greater than when the angle (bank angle) between the exposed surface 166a of the subchondral bone 166 and the edge 164a of the normal region 164 is more than 90° (see FIG. 9B).

With one ultrasonic treatment device 2 disposed in the inside portal, the surgeon can use the surgical system 1 to conduct a series of treatments to remove the treatment target part in the cartilage 112a of the femur 112 by the treatment portion 14 of the ultrasonic treatment device 2.

The surgeon has heretofore used, for example, an abrader bur or a shaver when conducting a treatment using the sharp curette to check the hardness of the cartilage 112a. Thus, in conventional treatments, different devices are used in the portal in turn. In the present embodiment, a series of treatments up to the use of the ultrasonic pick (another ultrasonic treatment device) 180 can be conducted by one ultrasonic treatment device 2, and the ultrasonic treatment device 2 does not need to be replaced in the portals. Therefore, the surgeon does not need to replace the treatment device 2 disposed in the articular cavity 136 during surgery, so that the surgery time can be reduced.

To cut the degenerated region 162, the surgeon uses the ultrasonic treatment device 2 and does not need to use a high-frequency device. If the high-frequency device is used to conduct a treatment, the surface 166a of the subchondral bone 166 might be invaded by heat. In contrast, when the ultrasonic treatment device 2 is used, heat invasion is less in the normal regions of the cartilages 112a, 114a, and 118a of the femur 112, the tibia 114, and the patella 118, and thermal necrosis in the cartilages 112a, 114a, and 118a can be prevented.

The cutting by the treatment portion 14 which ultrasonically vibrates is not a treatment by a heat source such as an electric scalpel. Therefore, this surgery permits a treatment to be conducted without the increase of temperature in the treatment target part, and does not thermally damage the treatment part.

The removal treatment is conducted by micro vibration of the treatment portion 14 of the ultrasonic treatment device 2. Therefore, the surgeon can adjust the cutting amount by the degree at which the treatment portion 14 is pressed to the part to be resected, and can freely adjust a cutting/amputation treatment which presses hard and a flattening treatment which weakly holds and flattens a surface to be resected, thereby achieving, for example, effective resection and cutting.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An arthroscopical surgical method using a first ultrasonic treatment device for a joint, the method comprising:
    transmitting ultrasonic vibration to a first treatment portion of the first ultrasonic treatment device;
    removing an injured region of an articular cartilage so that a subchondral bone is exposed and formed as a bottom surface;
    forming a cartilage edge that is nearly angled at 90 degrees with an exposed surface of the subchondral bone to form a pool-shaped depression;
    forming a hole by transmitting ultrasonic vibration to a second treatment portion of a second ultrasonic treatment device, the hole piercing up to a cancellous bone of the subchondral bone through the depression;
    scratching blood vessels in the cancellous bone;
    causing bleeding from the blood vessels so that blood is retained in the depression via the formed hole; and
    illuminating, using an infrared light source, the blood vessels with infrared light through the formed hole and checking the bleeding from the blood vessels under infrared observation.

2. The method according to claim 1, further comprising:
    before removing the injured region of the articular cartilage, administering a fluorescent chemical agent into the joint,
    observing the injured region of the articular cartilage by infrared light from the infrared light source, and
    switching the infrared light to visible light so that a surgeon recognizes a boundary of the injured region.

3. The method according to claim 2, further comprising:
    after forming the depression, observing by the infrared light whether there is any residual of the injured region of the articular cartilage, and
    when there is a residual of the injured region, transmitting ultrasonic vibration to the first treatment portion of the first ultrasonic treatment device and removing the residual of the injured region.

4. The method according to claim 1, wherein the second treatment portion is a boring portion.

\* \* \* \* \*